United States Patent [19]

Shirai et al.

[11] Patent Number: 4,771,105

[45] Date of Patent: Sep. 13, 1988

[54] WATER-ABSORBENT RESIN AND PROCESS FOR PRODUCING THE SAME

[75] Inventors: Hideharu Shirai, Nara; Fumito Yamai, Kusatsu; Setsuo Inada, Nara; Hisashi Ike, Nara; Yoshifumi Nakahara, Nara, all of Japan

[73] Assignee: Sekisui Kaseihin Kogyo Kabushiki Kaisha, Nara, Japan

[21] Appl. No.: 10,666

[22] Filed: Feb. 4, 1987

[30] Foreign Application Priority Data

Feb. 5, 1986 [JP] Japan .................................. 61-23462
Dec. 27, 1986 [JP] Japan ................................ 61-314449

[51] Int. Cl.$^4$ ................................................ C08F 8/42
[52] U.S. Cl. ............................ 525/54.23; 525/54.26; 525/330.1; 525/330.2; 525/370; 525/371; 525/372
[58] Field of Search ............... 525/330.1, 330.2, 54.23, 525/54.26

[56] References Cited

U.S. PATENT DOCUMENTS

| | | | |
|---|---|---|---|
| 3,779,952 | 12/1973 | Leonard, Jr. ................... | 525/330.2 |
| 3,802,912 | 4/1974 | Otocka .............................. | 525/330.2 |
| 4,027,082 | 5/1977 | Gavrilova et al. ............... | 525/330.2 |
| 4,076,663 | 2/1978 | Masuda et al. ................... | 128/284 |
| 4,090,013 | 5/1978 | Ganslaw et al. ................. | 526/15 |
| 4,401,795 | 8/1983 | Herman et al. ................... | 525/330.2 |
| 4,558,091 | 12/1985 | Hubbard ............................ | 524/734 |

FOREIGN PATENT DOCUMENTS 51-107389 9/1976 Japan .

Primary Examiner—Joseph L. Schofer
Assistant Examiner—Bernard Lipman
Attorney, Agent, or Firm—Armstring, Nikaido, Marmelstein & Kubovcik

[57] ABSTRACT

A water-absorbent resin of polyacrylic acid series characterized in that the resin has the crosslinked surface formed by reacting a powdery water-absorbent resin of polyacrylic acid series with an aluminum compound which can react with the powdery resin in the presence of polyhydric alcohol and water.

9 Claims, No Drawings

WATER-ABSORBENT RESIN AND PROCESS FOR PRODUCING THE SAME

BACKGROUND OF THE INVENTION

This invention relates to a water-absorbent resin and a process for producing the same. This invention relates, more particularly, to a water-insoluble, water-absorbent resin of polyacrylic acid type whose water-absorbing capability is improved.

Water-absorbent resins capable of highly absorbing water as water-absorbent and water-retentive materials have been currently used in such fields as sanitary supplies, medical supplies, cosmetics, agriculture, foods, civil engineering and construction, and household goods, As disclosed in U.S. Pat. Nos. 4,076,663 and 4,090,013, such water-absorbent resins include crosslinked polyethylene oxide, crosslinked polyvinyl alcohol, crosslinked polyacrylic acid and its salt, cellulose-acrylic acid-grafted copolymer and its salts, and hydrolyzates of starch-acrylonitrile-grafted copolymers, of which the water-absorbent resins of polyacrylic acid series have been widely used because of their excellent water-absorbing capability in terms of water absorption and the rate of water absorption.

Such water-absorbent resins of polyacrylic acid type have been utilized in the form of a powder which is produced by mechanically powdering a block of polymer obtained by polymerization in order to increase the rate of water absorption. In consideration of the fact that, in particular, water-absorbent resins with a high rate of water absorption have currently been required, the resins with a larger surface obtained by pulverization are used because the rate of water absorption of water-absorbent resins is proportional to their surface area. However, the pulverization by mechanically powdering means causes water-absorbent resins to be cut in crosslink or to develop a solubilizate fraction, leading to an extremely deteriorated water-absorbing capability such as water absorption capacity and the rate of water absorption. The pulverization also causes the a problem that a film is liable to develop on the particle surface in contact with water, which impedes water penetration and causes powder coagulation (a phenomenon of undissolved lump of flour) when water absorbing, resulting in an insufficient water-absorbing capability. For example, if a commercially available powdery water-absorbent resin is further mechanically powdered, its water-absorbing capability is deteriorated such that water absorption capacity is lowered by about a half and it takes a time as long as 30 minutes to 24 hours to obtain a given water absorption with respect to the rate of water absorption, causing the phenomenon similar to an undissolved lump of flour to be developed. Such powdering to improve the rate of water absorption has been accompanied by the disadvantage that some solubilization occurs or the phenomenon similar to an undissolved lump of flour occurs due to cross-link cutting, both of which extremely deteriorate the water-absorbing capability.

In Japanese Pat. Application laid open No. 168921/1982, a water-absorbent resin produced by coating a highly-water-absorbent macromolecular material such as cross linked polyacrylic acid salt, etc. with a water-soluble resin such as polyethylene glycol, etc. is disclosed which avoids the above-noted disadvantage and which generates no phenomenon similar to an undissolved lump of flour and has a high rate of water absorption. However, when the resin is produced, it involves a uneconomical production process wherein the highly-water-absorbent macromolecular material powder is coated with the water-soluble resin dissolved in a large amount of an organic solvent such as methanol, etc. and then the large amount of the solvent is removed in vacuo, and it is difficult to safely produce the material industrially because of the utilization of a flammable organic solvent. When water was used instead of an organic solvent such as methanol, etc. and the highly-water-absorbent macromolecular material powder was coated with a mixture of water and polyethylene glycol, the resultant water-absorbent resin generated the phenomenon similar to an undissolved lump of flour and failed to increase the rate of water absorption.

In Japanese Pat. Application laid open No. 42602/1983, a method is disclosed which increases the rate of water absorption and prevents the phenomenon similar to an undissolved lump of flour by dispersing a hydrophilic-crosslinked polymer into a dispersing medium such as methanol or ethanol to further crosslink the resin surface with a crosslinking agent such as multivalent metal salt. However, even with that method, an uneconomical production process is required where the resin is surface treated using a large amount of a solvent such as methanol, ethanol, etc., filtered, and then vacuum dried for a long time to remove the solvent, leading to an insufficient improvement of the rate of water absorption and insufficient prevention of the phenomenon similar to an undissolved lump of flour when using only the crosslinking agent such as multivalent metal salt.

Further, a water-absorbent resin is required to have such properties as a high gel strength after water absorbing and an excellent resin fluidity before water absorbing with regard to a workability when the end product using the water-absorbent resin is produced as well as an excellent water absorption and the speed of water absorption. However, no prior water-absorbent resin of polyacrylic acid series has sufficiently satisfied these requirements.

SUMMARY OF THE INVENTION

It is accordingly an object of this invention to provide a water-absorbent resin having a highly-water-absorbing capability. More particularly, it is an object of this invention to provide a water-absorbent resin having a high-water-absorption capacity and/or a high-rate of water absorption.

Another object of this invention is to provide a process for producing a water-absorbent resin having a highly-water-absorbing capability.

This invention, which has been completed as a result of an extensive research by the inventors, is directed to the provision of a water-absorbent resin of polyacrylic acid type characterized in that the resin has a crosslinked surface formed by reacting a powdery water-absorbent resin of polyacrylic acid type with aluminum compounds which can react with the resin in the presence of a polyhydric alcohol and water, and to the provision of a process for producing the same.

The water-absorbent resin of this invention is characterized in that it generates no phenomenon similar to an undissolved lump of flour when water absorbing, has a high gel strength after water absorbing, and has a high resin fluidity before water absorbing.

The production method of the water-absorbent resin of this invention is further characterized in that it provides a water-absorbent resin having a highly-water-absorbing capability by a simple method without using an organic solvent such as lower alcohol.

DETAILED DESCRIPTION OF THE INVENTION

Examples of the water-absorbent resins of polyacrylic acid type used in this invention as a raw material include polymers or copolymers whose main chain has at least a monomer unit of acrylic acid and/or acrylic acid salt; polysaccharide such as starch and cellulose-acrylic acid grafted copolymer and its salt, and the like.

The polymers or copolymers whose main chain has at least a monomer unit of acrylic acid and/or acrylic acid salt include polyacrylic acid, polyacrylic acid salt, and acrylic acid-acrylic acid salt copolymer. Examples of the salt moieties of the acrylic acid salt and polyacrylic acid salt can include alkali metal salts such as sodium salt, potassium salt, lithium salt, etc. and organic base salts such as ammonium salt, triethylamine salt, pyridine salt, etc. These polymers may be the copolymers with acrylamide, N-vinyl pyrrolidone, 2-hydroxyethyl methacrylate, etc., in order to modify the characteristics such as the degree of water uptake as required. The raw polymers are preferably crosslinked ones which are produced by known crosslinking means. For example, the crosslinked copolymers are produced by crosslinking themselves by heating, by using a catalyst having an oxidative property such as potassium persulfate and the like, or by adding a crosslinking agent having two or more polymerizable unsaturated bonds such as N, N'-methylene-bis-acrylamide when performing polymerization. Those resins are usually produced by polymerization, as required, after adding the crosslinking agent and, other copolymerizable monomers to a water solution of acrylic acid and/or acrylic acid salt, and then are dried to form blockish resins which are then powdered to an appropriate size by a grinder. The grain size is preferably 5 to 400 mesh and more preferably 10 to 200 mesh in terms of Tyler's standard sieve mesh. If the resins are produced by emulsion polymerization or suspension polymerization, small spherical particle polymers can be obtained. They may further be powdered.

Polysaccharide such as starch and cellulose-acrylic acid grafted copolymers and their salts can be produced by conventional methods, for example, by the method disclosed in U.S. Pat. No. 4,076,663.

The water-absorbent resin of this invention has a crosslinked surface which is formed by reacting the powdery water-absorbent resin mentioned above with an aluminum compound that can react with the powdery resin in the presence of a polyhydric alcohol and water.

Examples of the polyhydric alcohol to be used in this invention are as follows: diol group including ethylene glycol, 1,2-propanediol, 1,3-propanediol, butanediols (such as 1,2-butanediol, 1,3-butanediol, 1,4-butanediol, 2,3-butanediol, etc.), pentanediols (such as 1,5-pentanediol, 1,3-pentanediol, 2,3-pentanediol, etc.), hexanediols (such as 1,6-hexanediol, 2,5-hexanediol, etc.), 2-methyl-2,4-pentanediol, 2-methyl-2,3-butanediol, etc.; triol group including glycerin, trimethylolpropane, hexanetriols (such as 1,2,6-hexanetriol, 1,3,5-hexanetriol, etc.), triethanolamine, etc.; tetraol group including pentaerythritol, diglycerin, etc.; pentaol group including glucose, furanose, etc.; hexaol group including sorbitol, mannitol, etc.; octaol group including sucrose, etc.; lower alkylene oxide addition product of the compounds mentioned just above; and lower alkylene oxide copolymers. These polyhydric alcohols may be used by mixing two or more types of them. The lower alkylene oxides include alkylene oxides having 2 to 4 carbon atoms such as ethylene oxide (hereinafter referred to as EO), propylene oxide (hereinafter referred to as PO), butylene oxide, etc. Examples of polyhydric alcohols to which these alkylene oxides are added are as follows: diethylene glycol, triethylene glycol, polyethylene glycols [mean molecular weight (hereinafter referred to as MW): 200, 300, 400, 600, 1000, 2000, 6000, etc.], dipropylene glycol, tripropylene glycol, polypropylene glycols [MW: 200, 400, 1000, 2000, 4000, etc.], glycerin-EO addition products [MW: 400, 600, 1000, 3000, 4000, etc.], glycerin-PO addition products [MW: 400, 600, 1000, 3000, 4000, etc.], glycerin-EO (50)/PO(50) random addition products [MW: 2600, etc.], glycerin-PO(80)-EO(20) block addition products [MW: 3000, etc.], trimethylolpropane-EO addition product, trimethylolpropane-PO addition product, pentaerythritol-EO addition product, pentaerythritol-PO addition product, and sorbitol-EO addition product, etc. The lower alkylene oxide copolymers include random copolymer and block copolymer, such as polypropylene glycol-EO addition products [MW: 2400, 3100, 4000, etc.].

Among these compounds, for example, glycerin-EO(50)/PO(50) random addition product denotes the compound in which a mixture containing 50% EO and 50% PO by weight (each % by weight being with reference to total alkylene oxide weight) is randomly added to glycerin, and glycerin-PO(80)-EO(20) block addition product denotes the compound in which PO of 80% by weight is added to glycerin and then EO of 20% by weight is added to the product (each % by weight having the same meaning as defined above).

Preferable compounds among the polyhydric alcohols are ethylene glycol, propanediol, butanediol, pentanediol, hexanediol, 2-methyl-2,4-pentanediol, hexanetriol, glycerin, pentaerythritol, sorbitol, polyethylene glycol, polypropylene glycol, glycerin-EO addition product, glycerin-PO addition product, pentaerythritol-EO addition product, pentaerythritol-PO addition product, and sorbitrol-EO addition product, and more preferable compounds among them are ethylene glycol, propanediol, butanediol, pentanediol, hexanediol, 2-methyl-2,4-pentanediol, hexanetriol, and polyethylene glycol.

The added quantity ratios of the polyhydric alcohols to the water absorbent resins range from 0.01 to 50% by weight, preferably from 0.1 to 20% by weight, and more preferably from 1 to 15% by weight. An added quantity ratio less than 0.01% by weight provides no addition effect, while an added quantity ratio exceeding 50% by weight causes lowered water absorption capability or reduced power fluidity to provide an undesirable performance.

Experiments have shown that the water-absorbent resin of the invention produced using a compound, among the polyhydric alcohols, to which lower alkylene oxide was not added had an extremely good fluidity of the resin before water absorbing.

Aluminum compounds to be used as a crosslinking agent for the surface of water-absorbent resins of polyacrylic acid type in this invention may be the aluminum compounds which can react with the carboxyl group or carboxylate group of said water-absorbent resins, including aluminum salt such as aluminum chloride, aluminum nitrate, aluminum sulfate, aluminum phosphate, aluminum acetate, etc., aluminum hydroxide, aluminum alkoxide such a aluminum isopropoxide, aluminum ethoxide, aluminum-tertiary-butoxide, etc., two or more types of which may be mixed for use. Using aluminum compounds particularly in such state as aluminum hydroxide sol or aluminum hydroxide gel immediately after precipitation for crosslinking reaction enhances reactivity to allow the gel strength to increase without significantly deteriorating the water absorption properties and can avoid the formation of unnecessary residues, providing a preferable condition. This condition can suitably be obtained by the reaction of aluminum salt with aluminate or by the reaction of aluminum salt with alkali metal hydroxide in the presence of water.

The aluminum compounds are added to water-absorbent resins in added quantity ratios of 0.1 to 40% by weight, preferably 0.5 to 25% by weight, and more preferably 1 to 15% by weight. An added quantity ratio less than 0.1% by weight gives insufficient crosslinking to prevent the phenomenon similar to an undissolved lump of flour, while a ratio exceeding 40% by weight gives an excessive surface crosslinking, resulting in lowered water absorption.

The water to be used in this invention, which is not particularly specified, may be ion exchanged water, distilled water, city water, etc., and the quantity of water to be used should be sufficient to dissolve or disperse the aluminum compound, usually about 1 to 10 times the quantity of aluminum compound (by weight), preferably 1 to 8 times, and more preferably 2 to 6 times.

The water-absorbent resin in this invention is produced by treating a powdery water-absorbent resin of polyacrylic acid series with the aluminum compound which can react with said powdery resin in the presence of the polyhydric alcohol and water to crosslink the surface of said water-absorbent resin. More particularly, for example, the resin is produced by mixing said powdery water-absorbent resin of polyacrylic acid type with the aluminum compound in the presence of the polyhydric alcohol and water. The mixing means, which is not particularly limited, can use such conventional mixers as Nauta mixer, ribbon blender, conical blender, Henshel mixer and Raikai mixer. For example, the water-abosrbent resin is produced by such a method that said resin is added into a mixer, and solution in which a desired quantity of the polyhydric alcohol and the aluminum compound is dissolved (or dispersed) in water is admixed or sprayed in the mixer while stirring to provide a sufficient mixing, and finally the resultant mixture is dried by a dryer. A method may be used that respective water solutions (or dispersed solutions) for polyhydric alcohol and for aluminum compound are prepared, and both the solutions are simultaneously added to said resin, or either polyhydric alcohol solution or aluminum compound solution is added and then the remaining solution is added to said resin.

In the above production processes, the reaction temperature, which is not particularly limited, is usually from room temperature to 100° C., and preferably from room temperature to 60° C., and the reaction time is 1 to 120 minutes, and preferably 2 to 30 minutes. Drying is performed by using such conventional dryers as circulating hot air dryer and vacuum dryer, and the drying temperature is from room temperature to 150° C., and preferably from 70 to 120° C. In order to improve the fluidity and crosslinking properties while stirring, calcium chloride and zinc nitrate may be added to the mixture.

The most preferable, practical procedures of the preparation method of the crosslinking agent solution used for producing the water-absorbent resin in this invention are as follows:

(A) Where aluminum chloride and sodium aluminate are used as aluminum compounds:
  (1) Eight parts by weight of aluminum chloride hexahydrate is added to 85 parts by weight of water while stirring to effect dissolution.
  (2) Then, 8 parts by weight of sodium aluminate is gradually added while stirring.
  (3) Aluminum hydroxide is at once formed to give a cloudy appearance to the mixture, and the viscosity rapidly increases to cause a loss of the fluidity, but continuing stirring causes the mixture to have again the fluidity, becoming a viscous solution. A stirring time more than 20 minutes is usually preferable.
  (4) Fifteen parts by weight of the polyhydric alcohol is added to the solution, and stirred to obtain an uniform solution, allowing the crosslinking agent solution to be prepared. The polyhydric alcohol may be added to the original water.

(B) Where aluminum chloride and alkali metal hydroxide such as sodium hydroxide are used as an aluminum compound:
  (1) Fifteen and nine tenths parts by weight of sodium hydroxide is dissolved in 85 parts by weight of water.
  (2) Then, 32 parts by weight of aluminum chloride hexahydrate is gradually added while stirring.
  (3) The subsequent procedures are performed in a similar manner to (3) and (4) of the method (A) mentioned above.

The crosslinking agent solution prepared in such manners is used preferably in the ratio of 100 to 300 parts by weight of powdered water-absorbent resin of polyacrylic acid series to 100 parts by weight of said solution. Since, if the crosslinking agent solution is left to stand, aluminum hydroxide precipitates to be separated from the solution, the solution is used preferably in a stirred and dispersed state.

The water-absorbent resins of this invention are used in the form of a powder, whose grain size is about 5 to 500 mesh, and preferably 10 to 200 mesh in terms of Tyler's standard sieve mesh. The resins may be used, as required, containing such admixtures as fluidity assisting agents including finely powdered silica and talc, bulking filter, antioxidant, fungicide, bactericide, perfume, colorant, and deodorant. The water-absorbent resins of this invention can be used in a similar manner to prior water-absorbent resins.

This invention has various features, for example:
(1) The water-absorbent resins of this invention exhibit a high water absorption capacity and high rate of water absorption not only for aqueous water but also for solutions containing salts such as human body fluids including urine and blood. Prior water-absorbent resins have limited utility in this respect because of low water absorption capability for salt solutions, while the water-absorbent resins of this invention can quickly absorb the urine and blood. A high gel strength after water absorbing allows said resins to retain water content in a stable shape, providing an excellent water retention characteristics.

(2) The water-absorbent resins of this invention generate no phenomenon similar to an undissolved lump of flour when water absorbing, permitting the rate of water absorption to extremely increase.

(3) Prior water-absorbent resins, which lack fluidity in the dry state, have involved various problems such as clogging of feeding ports with the resins or difficulty in producing an uniform spraying of the resins onto products when producing the end products using water-absorbent resins, such as paper diapers and sanitary napkins, while the water-absorbent resins of this invention, which exhibit a high fluidity before water absorbing, have an advantage of excellent workability.

(4) The process for producing the water-absorbent resins of this invention makes it possible to produce the water-absorbent resins having an excellent water absorption capability in a simple and economical manner. This means that prior production methods use a large quantity of organic solvent such as alcohol having combustible, explosive and toxic properties in coating and crosslinking processes, and require filtering, drying and solvent recovering processes; while the production method of this invention, which uses no organic solvent and provides the water-absorbent resins in a simple operation, offers a simple production process and reduced cost, and can safety produce the water-absorbent resins on an industrial scale.

The water-absorbent resins of this invention have high water absorption capacity and high rate of water absorption as well as an excellent water retention characteristics and gel strength. They, therefore, can be utilized for various application, for example, sanitary supplies such as paper diapers, catamenial tampons, sanitary napkins and paper towels, medical supplies such as water retainers of cataplasm, agricultural supplies such as seen germination assisting agents and soil water retainers, building supplies such as dew condensation preventing materials for interior portions, and cosmetics supplies such as water retainers of cosmetics and perfumes.

EXAMPLES

Hereinafter, this invention will be described in greater detail with reference to Comparative Examples and Examples. However, this invention is not limited to these Examples. Percent in the Examples is by weight unless otherwise specified.

The tests of water-absorbent resins were conducted in the following methods:

(a) measurement of water absorption

A sample (Xg) is put into a commerically available coffee filter, which is folded, and dipped into a 0.9% saline solution for a given time, and then the weight (Yg) including the coffee filter is measured. With the weight (Zg) of the wet coffee filter itself measured beforehand, the water absorption capacity is determined by the following equation:

$$\text{Water absorption capacity} = (Y-Z)/X$$

(b) Measurement of gel strength

Ninety eight grams of a 0.9% saline solution is added to a 200 ml beaker to effect gel formation through addition of 2 g of a water-absorbent resin while stirring by a magnetic stirrer. After the resultant gel has been left to stand for 24 hours, the steel balls of the ball bearings to JIS Standard whose diameter increases by 1/16 inch increments from a 3/16 inch diameter are sequentially placed on the gel surface until they settle in the gel. However, the ball having not settled is removed before the subsequent ball is placed. With such procedures, the maximum diameter of the ball which does not settle is defined as the gel strength of the resin.

(c) Measurement of fluidity

Using a hollow cylindrical vessel (with an inside diameter of 43 mm) having a bottom plate whose center part has a circular hole (with a diameter of 15 mm), 150 ml of a dry water-absorbent resin is added to the vessel with the circular hole closed. Then the circular hole is opened to allow the water-absorbent resin to flow out. After the flow has ended, the angle formed by the surface of the residual resin in the vessel and the bottom plate is measured, and the angle is defined as the fluidity of the resin.

COMPARATIVE EXAMPLE 1

A 20% water solution (25 parts by weight) of each aluminum compound shown in Table I was added with vigorous stirring to 100 parts by weight of the mechanically, finely-ground resin from a powdered water-absorbent resin [whose trade name: AQUAKEEP 10 SH, by Steel Chemical Co., Ltd. (Japan)] which is commercially available, self-crosslinking type resin of sodium polyacrylate type produced by a reverse phase suspension polymerization technique. After stirring for 2 to 3 minutes, the resin was dried to about 7% in water content. The water absorption characteristics test of each resin obtained in such manner was conducted. The results are shown in Table I.

As shown in Table I, if a water solution consisting of only an aluminum compound without containing any polyhydric alcohol is used, a water-absorbent resin is coagulated or bonded when mixing is performed the gel is difficult to knead, and the phenomenon similar to an undissolved lump of flour is likely to develop when water absorbing. The rate of water absorption is also insufficient.

TABLE I

| Aluminum compounds | Water absorption (capacity) Time (minute) | | | | Remarks |
| --- | --- | --- | --- | --- | --- |
| | 3 | 5 | 10 | 30 | |
| Aluminum isopropoxide | 20 | 40 | 60 | 70 (equilibrium) | Finely powdered granules are coagulated and bonded when mixing. |
| Sodium aluminate | 30 | 45 | 50 | 60 (equilibrium) | A phenomenon of undissolved lump of flour develops when water absorbing. |
| Aluminum chloride hexahydrate | 30 | 45 | 50 | 60 (equilibrium) | |
| Same weight mixture of sodium aluminate and aluminum chloride hexahydrate | 25 | 45 | 60 | 70 (equilibrium) | Finely powdered granules are coagulated and bonded when mixing. |
| Same weight mixture of sodium aluminate and calcium chloride hexahydrate | 25 | 40 | 50 | 60 (equilibrium) | A phenomenon of undissolved lump of fluor develops when water absorbing. |
| Same weight mixture of sodium aluminate | 25 | 40 | 50 | 60 | |

TABLE I-continued

| Aluminum compounds | Water absorption (capacity) Time (minute) | | | | Remarks |
|---|---|---|---|---|---|
| | 3 | 5 | 10 | 30 | |
| and zinc nitrate hexahydrate | | | | (equilibrium) | |

EXAMPLE 1

Aqueous solutions of polyethylene glycols and aluminum compounds where prepared as indicated in Table II and used to produce water absorbent resins according to the procedure described in Comparative Example 1. The water absorption capability of the resultant water-absorbent resins were measured. The results are shown in Table II. The mixture of the finely powdered water-absorbent resins granules as a raw material with the water solution was powdery without rapidly stirring, and the finely powdered granules were not coagulates and bonded, providing an extremely good mixing characteristics. Where particularly aluminum isopropoxide or the same weight mixture of sodium aluminate and sodium chloride as an aluminum compound was used, the state of the resin before being dried was nearly equal to that of the dried resin. The water retention characteristics of the resins after absorbing water were extremely good for each case.

WATER SOLUTION COMPOSITION

| | |
|---|---|
| Total quantity of aluminum compounds: | 20 parts by weight |
| Polyethylene glycol: | 8 parts by weight |
| Ion exchanged water: | 72 parts by weight |

EXAMPLE 2

Thirty grams of acrylic acid was neutralized with 75 g of a 20% water solution of sodium hydroxide, and at the same time was mixed with 0.9 g of acrylamide. Three grams of a 1% water solution of sodium dithionite as a catalyst was first added to the mixture, and after 30 seconds 2 g of a 1% water solution of potassium persulfate and 2 g of a 1% water solution of aluminum nitrate were added to the mixture, which was stirred for about 30 seconds and then was left to stand to effect polymerization. When the polymerization was performed, the system did not particularly indicated an increased temperature. The resultant polymer was hardened to a plate shape by being dewatered and dried in a circulating hot air dryer at 100° C. for 24 hours. Then, the hardened polymer was powdered to be sieved with a Tyler's standard sieve of 80 mesh.

One hundred parts by weight of a crosslinking agent compound with a composition shown in Table III was added to 100 parts by weight of the resultant powdery product passing through the 80 mesh sieve and was mixed together, and then the resultant powder was dewatered and dried in a circulating hot air dryer at 100° C. for 30 minutes. The water absorption capability of the resultant resin is as shown in Table III.

As Comparative examples 2 to 5, the data using the composition containing no polyethylene glycol, aluminum compound and the like are together shown in the Table.

TABLE II

| Example No. | Aluminum compounds | Type of polyethylene glycol (PEG) | Water absorption (equilibrium) |
|---|---|---|---|
| 1-1 | Aluminum isopropoxide | PEG 400 | 70~75 times (after 3 min.) |
| | | PEG 2000 | 70~75 times (after 3 min.) |
| | | PEG 6000 | 60 times (within 3 min.) |
| 1-2 | Sodium aluminate | PEG 400 | 65 times (after 5 min.) |
| | | PEG 2000 | 65 times (after 5 min.) |
| | | PEG 6000 | 50 times (within 3 min.) |
| 1-3 | Aluminum chloride hexahydrate | PEG 400 | 65 times (after 5 min.) |
| | | PEG 2000 | 65 times (after 5 min.) |
| | | PEG 6000 | 50 times (within 3 min.) |
| 1-4 | Same weight mixture of sodium aluminate and aluminum chloride hexahydrate | PEG 400 | 70~75 times (after 3 min.) |
| | | PEG 2000 | 70~75 times (after 3 min.) |
| | | PEG 6000 | 60 times (within 3 min.) |
| 1-5 | Same weight mixture of sodium aluminate and calcium chloride hexahydrate | PEG 400 | 60 times (after 3 min.) |
| | | PEG 2000 | 60 times (after 3 min.) |
| | | PEG 6000 | 50 times (within 3 min.) |
| 1-6 | Same weight mixture of sodium aluminate and zinc nitrate hexahydrate | PEG 400 | 60 times (after 3 min.) |
| | | PEG 2000 | 60 times (after 3 min.) |
| | | PEG 6000 | 50 times (within 3 min.) |
| 1-7 | Water solution of aluminum sol | PEG 400 | 85 times (within 2 min.) |
| | | PEG 2000 | 85 times (within 2 min.) |
| | | PEG 6000 | 70 times (within 2 min.) |

TABLE III

| | | Composition (weight ratio) | | | | Water absorption (capacity) Time (minute) | | | | | |
|---|---|---|---|---|---|---|---|---|---|---|---|
| | | Polyethylene glycol 400 | Ion exchanged water | Aluminum chloride hexahydrate | Sodium aluminate | 3 | 5 | 10 | 20 | 30 | 60 |
| Example 2 | | 3 | 17 | 0.30 | 0.33 | 30 | 36 | 50 | 55 | 58 | 61 |
| Comparative example No. | 2 3 | 3 — | 17 20 | — 0.30 | — 0.33 | The mixture exhibits a blocking (dumpling state), making measurement impossible. | | | | | |

TABLE III-continued

| | Composition (weight ratio) | | | | Water absorption (capacity) Time (minute) | | | | | |
|---|---|---|---|---|---|---|---|---|---|---|
| | Polyethylene glycol 400 | Ion exchanged water | Aluminum chloride hexahydrate | Sodium aluminate | 3 | 5 | 10 | 20 | 30 | 60 |
| 4 | 20 | — | 0.30 | 0.33 | — | — | 7 | 8 | 10 | 12 |
| 5 | — | — | — | — | 6 | 6 | 6 | 8 | 10 | 12 |

EXAMPLE 3

Thirty grams of acrylic acid was neutralized with 75 g of a 20% aqueous solution of sodium hydroxide, and at the same time was added 0.9 g of acrylamide with stirring. Three grams of a 1% water solution of potassium persulfate as a catalyst was added to the mixture, which was stirred for about 30 seconds and then was left to stand at 60° C. for 1 hour to effect polymerization. The resultant polymer was hardened to a plate shape by being dewatered and dried in a circulating hot air dryer at 100° C. for 24 hours. Then, the hardened polymer was powered to be sieved with a Tyler's standard sieve of 80 mesh.

One hundred and fifty parts by weight of the resultant powdered product passing through the 80 mesh sieve was charged into a Raikai mixer, and 75 parts by weight of a crosslinking agent with a composition shown below was added to the product while stirring and was mixed together for 20 minutes, and then the resultant powder in a wet state was dried in a circulating hot air dryer at 100° C. for 1.5 hours to obtain a water-absorbent resin.

CROSSLINKING AGENT COMPOSITION

| | |
|---|---|
| (1) Ion exchanged water: | 85 parts by weight |
| (2) Polyhydric alcohol: | 15 parts by weight |
| (3) Aluminum chloride hexahydrate: | 8 parts by weight |
| (4) Sodium aluminate: | 8 parts by weight |

The tests of the water absorption (rate of water absorption), the gel strength after water absorbing and the resin fluidity before water absorbing on the resultant water-absorbent resins were conducted. The results are shown in Table IV.

As Comparative example 6, a water-absorbent resin was produced in a similar manner to Example 3 using a compound having 100 parts by weight of ion exchanged water except the polyhydric alcohol in the crosslinking agent composition, and its water absorption capability was examimed. The results are shown in Table IV.

EXAMPLE 4

A water-absorbent resin was produced in a similar manner to Example 3 except that the crossliking agent composition shown in Table V was used. The tests of the water absorption (rate of water absorption), the gel strength after water absorbing and the resin fluidity before water absorbing on the resultant water-absorbent resins were conducted. The results are shown in Table V.

It will be apparent that the water-absorbent resins of this invention, as shown in Tables IV and V, exhibit an excellent property in terms of the gel strength after water absorbing and the fluidity of water-absorbent resins as well as in terms of water absorption and the speed of water absorption.

All the water-absorbent resins obtained in Comparative examples 1 to 6 have poor hydro-extraction properties to make a correct measurement of water absorption difficult, providing an approximate value for the units digit of the measured values of water absorption.

TABLE IV

| Example No. | Polyhydric alcohols | Water absorption (capacity) Time (minute) | | | | | | Gel strength (inch) | Fluidity (degree) |
|---|---|---|---|---|---|---|---|---|---|
| | | 3 | 5 | 10 | 20 | 30 | 60 | | |
| 3-1 | 1,3-butanediol | 57 | 60 | 63 | 66 | 66 | 67 | 10/16 | 36 |
| 3-2 | 1,5-pentanediol | 59 | 60 | 64 | 65 | 65 | 65 | 9/16 | 40 |
| 3-3 | 2-methyl-2-4-pentanediol | 61 | 63 | 63 | 63 | 64 | 64 | 8/16 | 37 |
| 3-4 | 1,2,6-hexanetriol | 56 | 57 | 59 | 59 | 59 | 60 | 9/16 | 40 |
| Comparative example 6 | — | 35 | 40 | 50 | | 60 | | 3/16 or less | |

TABLE V

| Example No. | Crosslinking agent composition Figures in parentheses indicate parts by weight. | | | Water absorption (capacity) Time (minutes) | | | | | | Gel strength (inch) | Fluidity (degree) |
|---|---|---|---|---|---|---|---|---|---|---|---|
| | | | | 3 | 5 | 10 | 20 | 30 | 60 | | |
| 4-1 | Water (85) | 1,3-butanediol (15) | AlCl₃.6H₂O (32) + NaOH (15.9) | 58 | 61 | 64 | 67 | 69 | 69 | 9/16 | 37 |
| 4-2 | Water (85) | 1,3-butanediol (15) | Al(OH)₃ (10) | 50 | 54 | 54 | 57 | 59 | 60 | 4/16 | 40 |
| 4-3 | Water (85) | 1,3-butanediol (15) | AlCl₃.6H₂O (31) | 49 | 52 | 53 | 55 | 57 | 57 | 5/16 | 42 |
| 4-4 | Water (85) | 1,3-butanediol (15) | Aluminum isopropoxide (26) | 54 | 57 | 60 | 62 | 64 | 66 | 5/16 | 41 |
| 4-5 | Water (85) | Polyethylene glycol (MW 2000) (15) | AlCl₃.6H₂O (8) + NaAlO₂ (8) | 57 | 60 | 64 | 68 | 68 | 70 | 8/16 | 58 |

What is claimed is:

1. A water-insoluble, water absorbent resin comprising a polymer of acrylic acid, a polysaccharide-acrylic acid graft copolymer, or a copolymer of acrylic acid with a monomer selected from the group consisting of acrylamide, N-vinyl-pyrrolidone and 2-hydroxyethyl methacrylate, or a salt thereof; said resin having a crosslinked surface formed by reacting the resin having a particle size of 5 to 400 mesh with between 0.1 and 40% by weight of an aluminum compound selected from the group consisting of aluminum salts, aluminum hydroxides and aluminum alkoxides; in the presence of between 0.01 and 50% by weight of a diol selected from the group consisting of ethylene glycol, propanediol, butanediol, pentanediol, hexanediol, 2-methyl-2,4-pentanediol, polyethylene glycol, and polypropylene glycol; and water; and drying the resin having its surface crosslinked by reaction with said aluminum compound.

2. A water-absorbent, polyacrylic acid-based resin according to claim 1, wherein said aluminum compound is at least one member selected from the group consisting of aluminum chloride, aluminum nitrate, aluminum sulfate, aluminum phosphate, aluminum hydroxide, aluminum isopropoxide, aluminum ethoxide and aluminum-tert-butoxide.

3. A water-absorbent, polyacrylic acid-based resin according to claim 2, wherein said aluminum compound is aluminum hydroxide.

4. A water-absorbent, polyacrylic acid-based resin according to claim 3, wherein said aluminum hydroxide is an aluminum hydroxide gel formed by the reaction of an aluminum salt with an aluminate salt.

5. A water-absorbent, polyacrylic acid-based resin according to claim 3, wherein said aluminum hydroxide is an aluminum hydroxide gel formed by the reaction of an aluminum salt with an alkali metal hydroxide.

6. A water-absorbent, polyacrylic acid-based resin according to claim 1, wherein said resin is a resin selected from a group consisting of polysaccharide-acrylic acid graft copolymers and their salts.

7. A water-absorbent, polyacrylic acid-based resin according to claim 1, wherein said polyhydric alcohol is added in an amount between 0.1% and 20% by weight, based upon the weight of polyacrylic acid and said aluminum compound is added in an amount between 0.5% and 25% based upon the weight of polyacrylic acid.

8. A water-absorbent, polyacrylic acid-based resin according to claim 1, wherein said polyhydric alcohol is added in an amount between 1% and 15% by weight, based upon the weight of polyacrylic acid and said aluminum compound is added in an amount between 1% and 15% based upon the weight of polyacrylic acid.

9. A process for the production of a water-insoluble, water absorbent resin, which comprises crosslinking the surface of a polymer of acrylic acid, a polysaccharide-acrylic acid graft copolymer, or a copolymer of acrylic acid with a monomer selected from the group consisting of acrylamide, N-vinyl-pyrrolidone and 2-hydroxyethyl methacrylate, or a salt thereof; by reacting the polymer having a particle size of 5 to 400 mesh with between 0.1 and 40% by weight of an aluminum compound selected from the group consisting of aluminum salts, aluminum hydroxides and aluminum alkoxides; in the presence of between 0.01 and 50% by weight of a diol selected from the group consisting of ethylene glycol, propanediol, butanediol, pentanediol, hexanediol, 2-methyl-2,4-pentanediol, polyethylene glycol, and polypropylene glycol; and water, and drying the resin reacted with said aluminum compound.

* * * * *